United States Patent [19]

Lover et al.

[11] 4,238,499

[45] Dec. 9, 1980

[54] METHOD OF KILLING ECTOPARASITES WITH IMIDAZOLINE AND IMIDAZOLIUM TOXICANTS

[75] Inventors: Myron J. Lover, Moutainside; Arnold J. Singer, Verona; Donald M. Lynch, Waldwick, all of N.J.

[73] Assignee: Block Drug Company Inc., Jersey City, N.J.

[21] Appl. No.: 12,509

[22] Filed: Feb. 15, 1979

[51] Int. Cl.$^2$ ............................................. A01N 9/22
[52] U.S. Cl. .................................. 424/273 R; 424/70; 424/71; 424/358; 424/362; 548/341
[58] Field of Search ..................... 424/273 R; 548/341

[56] References Cited

U.S. PATENT DOCUMENTS

| | | | |
|---|---|---|---|
| 2,215,861 | 9/1940 | Waldmann et al. | 548/341 |
| 2,215,863 | 9/1940 | Waldmann et al. | 548/341 |
| 2,369,817 | 2/1945 | De Groote et al. | 260/404.5 PA |
| 2,379,413 | 7/1945 | Bradley | 260/404.5 PA |
| 2,392,326 | 1/1946 | Kyrides | 548/341 |
| 2,820,043 | 1/1958 | Rainey et al. | 548/341 |
| 3,116,249 | 12/1963 | Ralner et al. | 548/341 |
| 3,178,446 | 4/1965 | Sannicolo | 548/341 |

FOREIGN PATENT DOCUMENTS

| | | | |
|---|---|---|---|
| 1213413 | 3/1966 | Fed. Rep. of Germany | 548/341 |
| 1486817 | 5/1967 | France | 548/341 |
| 47-7176 | 9/1972 | Japan | 424/320 |

Primary Examiner—Dale R. Ore
Attorney, Agent, or Firm—Ostrolenk, Faber, Gerb & Soffen

[57] ABSTRACT

Certain imidazolines and imidazolium derivatives have been found to exhibit toxicant activity with regard to ectoparasites or their ova, and to other insect species. The insecticidal (including ovicidal, miticidal or aphicidal) activity can in some instances be amplified by the cojoint use of a lower alkanol.

13 Claims, No Drawings

METHOD OF KILLING ECTOPARASITES WITH IMIDAZOLINE AND IMIDAZOLIUM TOXICANTS

BACKGROUND OF THE INVENTION

There are only a relatively few ectoparasiticides which are commercially available today. The most popular pediculicidal toxicants are Lindane (gamma benzene hexachloride), Malathion [(S-1,2-dicarbethoxyethyl)-O,O-dimethyl phosphorodithioate], synergized pyrethrins and Cuprex (a combination of tetrahydronaphthalene, copper oleate and acetone, the acetone not asserted to be active). Sulphur and Lindane are the best known agents for scabies. Because of increased concern about the overall safety of some of the known ectoparasitic toxicants, the search for new, safe and effective ectoparasiticides has intensified recently.

Many species of insects encase their ova in protective sheaths which are impregnable to most toxicants. The gestation period of the egg is often relatively long in comparison to the life cycle of the adult forms. Thus, an agent effective only against adults must persist for the lifetime of the developing ovum or must be reapplied as successive hatchings occur. The ideal agent for treatment of ectoparasites should be active against the ova as well as the adult and nymphal forms, and should be relatively non-toxic to the host. Few agents are, however, so active.

The toxicants can be used in the form of shampoos or body washes. In contrast to agents used by inunction, compositions designed to be used as shampoos or body washes must fulfill certain criteria. For example, they must either exert their parasiticidal and/or ovicidal effects within a very short time or must resist washing off during the course of ablutions.

It has now been discovered that a small group of imidazolines and imidazolium derivatives are quite effective as toxicants for insects, particularly ectoparasites or their ova, and aphids. While it has been reported that some other imidazoline derivatives have some activity as insecticides (see U.S. Pat. Nos. 3,996,392 and 3,948,934) and the instant imidazolines are known to exhibit a mild germicidal, germistatic, fungicidal and fungistatic activity, the present imidazolines and imidazolium derivatives exhibit a surprising degree of toxicity against insects, particularly the ectoparasites and their ova, and aphids and such activity can, in some instances, be enhanced by the cojoint use of a lower alkanol.

Accordingly, it is the object of this invention to provide new, safe and effective toxicants for use against insects and their ova, particularly ectoparasites and their ova, and aphids. This and other objects of the invention will become apparent to those skilled in the art from the following detailed description.

SUMMARY OF THE INVENTION

This invention relates to insecticides and a method for controlling insects. More particularly, the invention relates to the use of certain imidazolines and imidazolium derivatives as toxicants for ectoparasites and/or their ova and/or aphids and to the toxicant compositions containing such imidazolines and imidazolium derivatives as toxicants.

DESCRIPTION OF THE INVENTION

The toxicants of the present invention are certain imidazolines and imidazolium derivatives which are represented by the formulas I and II respectively

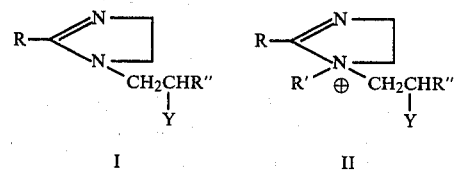

wherein R is alkyl of 6–20 carbon atoms, R' is carboxy lower alkyl or hydroxy lower alkyl, R" is hydroxy, carboxy lower alkoxy, sulfo lower alkoxy or amino, and Y is H or OH. Y is preferably OH when R" is sulfo lower alkoxy and preferably H in all other instances. In general, the reference to "lower" indicates about 1 to 4 carbon atoms. Thus, the R groups encompass such diverse moieties as heptyl, nonyl, heptadecenyl and can also be derived from naturally occurring materials such as being the alkyl chain from a coconut fatty radical mixture. Carboxy methyl, carboxy ethyl and hydroxy ethyl are typical of the carboxy lower alkyl and hydroxy lower alkyl radicals which constitute R'. Exemplary of the R" carboxy lower alkoxy, sulfo lower alkoxy and amino lower alkyl radicals include carboxy ethoxy, sulfo methyl and amino. The carboxy compounds can be employed as the acid or any pharmaceutically acceptable non-toxic salt. The imidazolium derivatives of the instant invention are known materials which are commercially available and have heretofore been used as amphoteric surfactants.

One or more of the imidazolines or imidazolium derivatives of the present invention can be incorporated into an active toxicant composition which can be in the form of a liquid, powder, lotion, cream, gel or aerosol spray, or foam as the result of formulation with inert pharmaceutically acceptable carriers by procedures well known in the art. Any pharmaceutically acceptable carrier, whether aqueous or non-aqueous, which is inert to the active ingredient can be employed. By inert is meant that the carrier does not have a substantial detrimental effect on the toxicant activity of the active ingredient. Aqueous pharmaceutically acceptable carriers are preferred.

The active imidazoline or imidazolium toxicants are incorporated into the toxicant compositions used to treat the animal or human host in need of such treatment, believed to be in need of such treatment, or desired to be prophylactically protected in an effective toxicant amount. By such amount is meant the amount which will cause at least 50% of the target organisms to die within 24 hours (or within two weeks in the case of the ova). The minimum concentration of imidazoline or imidazolium derivative required to provide an effective toxic amount varies considerably depending on the particular imidazoline or imidazolium derivative, the particular inert pharmaceutically acceptable carrier being employed and any other ingredients which are present. Thus, in one case, a 5% concentration may suffice, while in other cases, concentrations as high as 30% may be required to obtain an effective toxic dose. Usually, the imidazolines or imidazolium derivatives of the present invention will be present in concentrations of about 1–25%, and most preferably in concentrations of about 5–20%.

The instant imidazolines or imidazolium derivatives can also be employed as adjunct toxicants in a preparation which otherwise exhibits toxicant activity. In such preparations, the term "effective toxic dose" means that amount which will increase the mortality rate by at least about 20%.

A particularly desirable component in some of the compositions of this invention is one or more lower (1–8 carbon atom) aliphatic alcohols such as ethanol, isopropanol, pentanol and the like in an amount of about 5-90%, preferably about 20-30%. The lower alcohol surprisingly enhances the activity of the imidazoline and imidazolium derivative toxicants to a high degree.

The references to mortality herein have been made with regard to standard test procedures. When the ectoparasite is the human body louse, the standard mortality tests are the following two minute immersion tests:

Pediculicidal activity: A 50 ml beaker is filled with tap water and allowed to come to room temperature (about 24° C.). Ten young adult male and ten young adult female lice (*Pediculus humanus corporis*) of the same age group and from the same stock colony are placed on a 2×2 cm coarse mesh patch. The sample to be tested, maintained at room temperature, is shaken until homogeneous and placed into a 50 ml beaker. The mesh patch is placed into the sample immediately after pouring, allowed to submerge, and after two minutes is removed and immediately plunged into the beaker containing the tap water. The patch is vigorously agitated every ten seconds and after one minute the patch is removed and placed on paper toweling. The lice are then transferred to a 4×4 cm black corduroy cloth patch and this point of time is considered zero hours. Thereafter, the corduroy patch is placed in a petri dish which is covered and stored in a 30° C. holding chamber.

Ovicidal activity: 15 adult, 5 to 10 day old, female lice (*Pediculus humanus corporis*) are placed on a 2×2 cm nylon mesh patch which is placed in a petri dish, covered and maintained in an incubator at 30° C. for 24 hours. The adult lice are then removed and the number of plump, viable eggs and shriveled non-fertile eggs on the patch are recorded. The sample to be tested, maintained at room temperature, is shaken until homogeneous and poured into a 50 ml beaker. Immediately, after the pouring, the mesh patch is placed into the beaker, allowed to submerge, and after two minutes is removed and immediately plunged into a 50 ml beaker containing tap water at room temperature (about 24° C.). The patch is vigorously agitated every ten seconds and after one minute, the patch is removed and placed on paper toweling for one minute. The patch is then placed in a petri dish which is covered and stored in the 30° C. incubator. Fourteen days following treatment, the number of hatched eggs and the number of shriveled or unhatched eggs is noted.

For determining miticidal activity, the following procedure is used:

Into a one cubic foot chamber, held at room temperature, is placed a covered microscope depression slide containing ten adult mixed sex mites, *Psoroptes equi* var. *cuniculi.* The slide is positioned at a distance of ten inches horizontally and four inches below the activator of a mechanical spray device and uncovered. The mechanical pump spray device delivers 50 milligrams of sample per depression of the activator. The sample to be tested, maintained at room temperature, is shaken until homogeneous and placed in the mechanical pump spray device. The primed activator is depressed twice, releasing 100 milligrams of spray mist into the closed chamber. The mist is allowed to settle and the slide containing the mites is removed and covered. This point of time is considered zero hours. The covered slide is then held at room temperature for 24 hours. Microscopic observations are noted at 0, 1 and 24 hours post treatment. Controls are run in an identical manner as that described using water, and net mortality results are reported.

Aphicidal activity is determined as follows:

Into a 1 cubic foot chamber held at room temperature is placed a covered petri dish containing ten adult mixed sex aphids, *Macrosiphum euphorbiae.* The dish is positioned at a distance of ten inches horizontally and four inches below the tip of a mechanical spray device and uncovered. The mechanical spray pump device delivers 50 milligrams of sample per depression of the actuator. The sample to be tested, maintained at room temperature, is shaken until homogeneous and placed in the mechanical pump spray device. The primed pump is depressed once, the mist is allowed to settle, the petri dish containing the aphids is rotated 180° and the primed pump is depressed again. The mist is allowed to settle and the dish is removed and covered. This point of time is considered zero hours. The covered dish is held at room temperature for 24 hours and observations are noted at 0, 1 and 24 hours post treatment.

In all of the foregoing tests, controls are run in the identical manner to that described, with room temperature (24° C.) tap water substituted for the sample to be tested. The results of the tests reported are net results.

The pediculicidal, ovicidal and miticidal activity of various toxicants of the instant invention were tested in the two minute immersion tests described above. The concentration of the imidazolines and imidazolium derivatives which caused 50% mortality was determined in a system where the compound was mixed with water and the results are shown in the following Table 1.

TABLE 1

| R | R' | R'' | Y | Pediculicidal | Ovicidal | Miticidal |
|---|---|---|---|---|---|---|
| nonyl | $-CH_2CO_2-$ | OH | H | >30 | >35 | 9.1 |
| (1) | $-CH_2CO_2-$ | OH | H | 27 | >35 | 8.7 |
| (1) | $-CH_2CH_2CO_2-$ | OH | H | >40 | >40 | 13.8 |
| heptadecyl | $-CH_2CO_2-$ | OH | H | 3 | 13.1 | 1.6 |
| 8-heptadecenyl | $-CH_2CH_2CO_2-$ | OH | H | >35 | >35 | >15 |
| heptyl | $-CH_2CO_2-$ | $-OCH_2CO_2-$ | H | >35 | >35 | 7.5 |
| nonyl | $-CH_2CO_2-$ | $-OCH_2CO_2-$ | H | >15 | >35 | 8 |
| (1) | $-CH_2CH_2CO_2-$ | $-OCH_2CO_2-$ | H | >35 | >35 | 13.6 |
| 8-heptadecenyl | $-CH_2CH_2OH$ | $-CH_2SO_3-$ | OH | >25 | 12.4 | 8.4 |
| heptadecyl | $-CH_2CH_2OH$ | $-CH_2SO_3-$ | OH | >15 | >15 | 3.5 |
| (1) | $-CH_2CH_2OH$ | $-CH_2SO_3-$ | OH | >40 | >40 | 13.7 |
| decyl | (3) | $-OCH_2CH_2CO_2H$ | H | >35 | >35 | >15 |
| branched $C_{17}$ | (3) | $-OCH_2CH_2CO_2H$ | H | 5 | 8.5 | 10 |

TABLE 1-continued

| R | R' | R" | Y | Pediculicidal | Ovicidal | Miticidal |
|---|---|---|---|---|---|---|
| heptyl | (3) | OH | H | >15 | >20 | >15 |
| (1) | (3) | OH | H | 14 | >20 | >15 |
| branched $C_{17}$ | (3) | OH | H | 35 | 36 | >15 |
| 8-heptadecenyl | (3) | OH | H | 19 | >25 | >15 |
| 8-heptadecenyl | (3) | $NH_2$ | H | >15 | >15 | (2) |
| heptadecyl | (3) | $NH_2$ | H | >15 | >15 | (2) |

(1) derived from coconut fatty radical mixture
(2) insoluble at test concentrations
(3) monosubstuted at position #1, i.e., formula I The foregoing tests were repeated in a system where the imidazoline was mixed with 25% isopropanol and water q.s. ad. 100%. The results are shown in the following Table 2.

TABLE 2

| R | R' | R" | Y | Pediculicidal | Ovicidal | Miticidal |
|---|---|---|---|---|---|---|
| nonyl | $-CH_2CO_2-$ | OH | H | 12 | >35 | 3.5 |
| (1) | $-CH_2CO_2-$ | OH | H | 16 | >35 | >15 |
| (1) | $-CH_2CH_2CO_2-$ | OH | H | >40 | >40 | >15 |
| heptadecyl | $-CH_2CO_2-$ | OH | H | 6.8 | 12.3 | 1 |
| 8-heptadecenyl | $-CH_2CH_2CO_2-$ | OH | H | >35 | >35 | >15 |
| heptyl | $-CH_2CO_2-$ | $-OCH_2CO_2-$ | H | >35 | >35 | 5.5 |
| nonyl | $-CH_2CO_2-$ | $-OCH_2CO_2-$ | H | 15 | >35 | 4.6 |
| (1) | $-CH_2CH_2CO_2-$ | $-OCH_2CO_2-$ | H | >35 | >35 | >15 |
| 8-heptadecenyl | $-CH_2CH_2OH$ | $-CH_2SO_3-$ | OH | >25 | >25 | >15 |
| heptadecyl | $-CH_2CH_2OH$ | $-CH_2SO_3-$ | OH | 0.7 | >15 | 5 |
| (1) | $-CH_2CH_2OH$ | $-CH_2SO_3-$ | OH | >40 | >40 | 12.6 |
| decyl | (3) | $-OCH_2CH_2CO_2H$ | H | >15 | >35 | 14.2 |
| branched $C_{17}$ | (3) | $-OCH_2CH_2CO_2H$ | H | 11 | 18.5 | 13 |
| heptyl | (3) | OH | H | >15 | >20 | >15 |
| (1) | (3) | OH | H | 10 | 16 | 11.5 |
| branched $C_{17}$ | (3) | OH | H | 4.1 | 5.2 | 15 |
| 8-heptadecenyl | (3) | OH | H | 35 | 27 | 1 |
| 8-heptadecenyl | (3) | $NH_2$ | H | 6.8 | 6.4 | 12.2 |
| heptadecyl | (3) | $NH_2$ | H | 2.4 | 8.1 | 4 |

The aphicidal activity of two of the toxicants of the instant invention was determined according to the test protocol described above and the lethal concentration which caused a 50% mortality in a system which contained 25% isopropanol and water q.s. ad. 100% was determined. With the toxicant in which R was heptyl, R' carboxy methyl, R" carboxy methoxy and Y hydrogen, an $LC_{50}$ of 1.3 was found. When the compound was of Formula I, i.e., monosubstituted at the 1-position, and R was 8-heptadecenyl, R" hydroxy and Y hydrogen, an $LC_{50}$ of 1.2 was determined.

As previously indicated, the toxicants of the instant invention can be used in an adjunctive capacity. An example of such use is shown in Table 3.

TABLE 3

Adjunctive Toxicity

| | | % Mortality | |
|---|---|---|---|
| | %W/W | Pediculicidal | Miticidal |
| Isopropyl Alcohol | 25 | 100 | 0 |
| Stearamine Oxide | 10 | | |
| Cocoyl Sarcosine | 1 | | |
| Water | 64 | | |
| 4,5-dihydro-1-(1-hydroyethyl)-2-(8-heptadecenyl)-1H-imidazoline | 2 | 100 | 100 |
| Isopropyl Alcohol | 25 | | |
| Stearamine Oxide | 10 | | |
| Cocoyl Sarcosine | 1 | | |
| Water | 62 | | |

As noted above, various end use formulations can be prepared. Some typical formulations are set forth below and the amounts recited are percentages by weight:

| | % w/w |
|---|---|
| Pediculicidal and miticidal clear liquid suitable for mechanical pump spray application or inunction | |
| Isopropanol | 25.00 |
| Sodium 1-(carboxymethyl)-4,5-dihydro-2-heptadecyl-1-(2-hydroxyethyl)-1H-imidazolium | 16.25 |
| Water | 58.75 |
| Miticidal lotion | |
| Glyceryl monostearate | 8 |
| Sodium 1-(carboxyethyl)-2-coco-4,5-dihydro-1-(2-hydroxyethyl)-1H-imidazolium | 16 |
| Water | 76 |
| Pediculicidal and ovicidal gel | |
| Isopropanol | 25.0 |
| Sodium 4,5-dihydro-2-heptadecyl-(2-hydroxyethyl)-1-(2-hydroxy-3-sulfopropyl)-1H-imidazolium | 5.0 |
| carbomer | 0.5 |
| Triethanolamine | 0.5 |
| Hydroxyethyl cellulose | 0.5 |
| Sodium chloride | 0.5 |
| Water | 68.0 |
| Ovicidal shampoo | |
| Sodium 4,5-dihydro-2-(8-heptadecenyl)-1-(2-hydroxyethyl)-1-(2-hydroxy-2-sulfopropyl)-1H-imidazolium | 15.000 |
| Methyl paraben | 0.050 |
| Propyl paraben | 0.005 |
| Water | 84.945 |

Various changes and modifications can be made in the present invention without departing from the spirit and scope thereof. The various embodiments described herein were for the purpose of illustration only and were not intended to limit the invention. Unless otherwise specified, all temperatures have been in centigrade and all parts and percentages by weight throughout this specification and claims.

What is claimed is:

1. A method of controlling ectoparasites, their ova or aphids which comprises applying to an animal or human in need of such control, an effective toxic amount of at least one imidazoline or imidazolium derivative of the formulas I or II

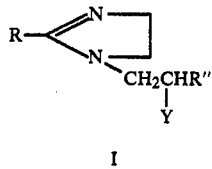 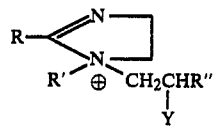

I   II where R is alkyl of 6 to 20 carbon atoms, R' is carboxy lower alkyl or hydroxy lower alkyl, R" is hydroxy, carboxy lower alkyl, sulfo lower alkoxy or amino and Y is hydrogen or hydroxy and the pharmaceutically acceptable non-toxic salts of the carboxy compounds.

2. The method of claim 1 wherein Y is hydrogen.

3. The method of claim 2 wherein R" is hydroxy.

4. The method of claim 2 wherein in formula II, R is heptadecyl, R' is —$CH_2CO_2$— and R" is hydroxy or in formula I, R is a branched 17 carbon atom alkyl radical, and R" is —$OCH_2CH_2CO_2$—.

5. The method of claim 1 wherein said derivative is employed in combination with an inert pharmaceutically acceptable carrier.

6. The method of claim 5 wherein said carrier is aqueous.

7. The method of claim 1 wherein said derivative is employed in combination with a lower aliphatic alcohol.

8. The method of claim 7 wherein said lower aliphatic alcohol is isopropanol.

9. The method of claim 8 wherein said derivative is a compound of formula I in which R is a branched 17 carbon atom alkyl radical, R" is —$OCH_2CH_2CO_2$— and Y is hydrogen; R is heptyl, a coconut fatty radical alkyl mixture or a branched 17 carbon atom alkyl chain, R" is hydroxy and Y is hydrogen; or R is heptadecenyl or heptadecyl, R" is $NH_2$ and Y is hydrogen; and the compounds of formula II in which R is heptadecyl or nonyl, R' is —$CH_2CO_2$—, R" is hydroxy and Y is hydrogen; or R' is —$CH_2CH_2OH$, R" is —$CH_2SO_3$, and Y is hydroxy and the pharmaceutically acceptable non-toxic salts of the carboxy compounds.

10. The method of claim 1, wherein said ectoparasites are lice.

11. The method of claim 1, wherein said ova are Pediculus ova.

12. The method of claim 1, wherein said ectoparasites are mites.

13. The method of claim 1, wherein said ectoparasites are aphids.

* * * * *